(12) United States Patent
Dafforn et al.

(10) Patent No.: US 8,754,168 B2
(45) Date of Patent: Jun. 17, 2014

(54) SOLUBILISATION OF MEMBRANE PROTEINS

(75) Inventors: Timothy Dafforn, Warwickshire (GB); Michael Overduin, West Midlands (GB); Timothy Knowles, West Midlands (GB)

(73) Assignee: The University of Birmingham (GB)

( * ) Notice: Subject to any disclaimer, the term of this patent is extended or adjusted under 35 U.S.C. 154(b) by 70 days.

(21) Appl. No.: 13/382,432

(22) PCT Filed: Jul. 8, 2010

(86) PCT No.: PCT/GB2010/001309
§ 371 (c)(1),
(2), (4) Date: Feb. 23, 2012

(87) PCT Pub. No.: WO2011/004158
PCT Pub. Date: Jan. 13, 2011

(65) Prior Publication Data
US 2012/0142861 A1 Jun. 7, 2012

(30) Foreign Application Priority Data

Jul. 8, 2009 (GB) .................................. 0911871.2
Apr. 9, 2010 (GB) .................................. 1005972.3

(51) Int. Cl.
*C08G 63/91* (2006.01)
(52) U.S. Cl.
USPC .......... 525/54.1; 525/190; 530/412; 530/422; 530/427

(58) Field of Classification Search
USPC .................. 525/54.1, 190; 530/412, 422, 427
See application file for complete search history.

(56) References Cited

FOREIGN PATENT DOCUMENTS

| GB | 2426703 A | 12/2006 |
|---|---|---|
| GB | 2426703 A | 12/2006 |
| WO | 2006129127 A1 | 12/2006 |

OTHER PUBLICATIONS

Knowles, T.J., et al.; Journal of the American Chemical Society, 2009, p. 7484-7485 and S1-S4.*
Belrhali, H., et al.; Structure, 1999, p. 909-917.*
British Search Report dated Dec. 4, 2009.
Abstracts from British Pharmacological Society Meeting entitled "3rd Focused Meeting Cell Signalling" held on Apr. 20-21, 2009 at the University of Leicester.
Third-party observations submitted in related European Patent Application No. 10733023.5 dated Jul. 11, 2013.
Poster referred to in third-party observations, Lin, et al., "Obtaining functional Human Adenosine 2a Receptor using Lipo-nano-disqs technology".

* cited by examiner

*Primary Examiner* — Robert Jones, Jr.
(74) *Attorney, Agent, or Firm* — Berliner & Associates

(57) ABSTRACT

A method is provided for solubilising a membrane protein. The method is applied to cellular material comprising the membrane protein and an associated membrane lipid. A copolymer of styrene and maleic acid, wherein the styrene: maleic acid ratio is between 1:2 and 10:1, is mixed with the cellular material to cause the copolymer, lipid and protein to form soluble macromolecular assemblies.

13 Claims, 2 Drawing Sheets

1. Polymer XZ-09-006 (6 kDa)
2. Polymer XZ-09-008 (10 kDa)
3. Polymer SZ33030 (30 kDa)
4. Polymer SZ42010 (10 kDa)
5. Polymer SZ28065 (65 kDa)
6. Polymer SZ28110 (110 kDa)
7. Polymer SMA 2000
8. Control: PagP without polymer
9. Control: PagP
10. Control: PagP
11. Control: PagP after dialysis
12. Standard protein marker

SOLUBILISATION OF MEMBRANE PROTEINS

The present application relates to solubilisation of membrane proteins. Such proteins are commonly found in the membranes of living cells.

The lipid bilayer membrane is a well known structure in molecular cell biology. These membranes are formed from a double layer of glycolipids and phospholipids; each phospholipid molecule has a hydrophilic polar head and a hydrophobic acyl tail, and the molecules in the bilayer are arranged in parallel, with the hydrophilic polar heads forming the inner and outer surfaces of the layer and the hydrophobic tails forming the interior of the layer. Other lipids such as sterols are also found in the lipid bilayer membrane. Such lipid bilayer membranes include cell membranes in both prokaryotes and eukaryotes, and the membranes surrounding many intracellular organelles in eukaryotes.

The present invention is particularly suitable for use with integral membrane proteins, i.e. any protein that crosses, or is embedded or integrated into such membranes, including G-protein coupled receptors (GPCRs), ion channels and transporters. Approximately one third of eukaryotic proteins are associated with membranes in this way, as are the targets of 40% of approved drugs. Integral membrane proteins typically have one or more regions which are hydrophobic and lie within the hydrophobic interior of the membrane bilayer, and one or more regions which are hydrophilic and extend out from the membrane. The hydrophilic regions may lie on either or both sides of the membrane.

GPCRs are a group of proteins characterised by containing seven transmembrane alpha-helices. The proteins fall into three general classes:class 1 (rhodopsin-related), class 2 (secretin-related) and class 3 (metabotropic glutamate receptor-related). There are also 'frizzled' and 'smoothened' GPCRs. GPCRs are found in all mammalian species, amongst others. In particular, GPCRs control many physiological processes, and are the targets of many drugs. They are therefore of considerable pharmacological importance. GPCRs are thought to exist in multiple distinct conformations which are associated with different pharmacological classes of ligand, such as agonists and antagonists, and to cycle between these conformations in order to function (Kenakin T. (1997) *Ann NY Acad Sci,* 812, 116-125).

As with all proteins, the function of an integral membrane protein is dependent on its three-dimensional conformation. This conformation is stabilised by hydrophobic interactions of embedded regions with the interior of the membrane bilayer, ionic interactions of the non-embedded regions of the protein with the polar phospholipid heads and the surrounding aqueous medium, and by interactions (both hydrophobic and ionic) within the protein itself. Typical functions of membrane proteins include the transport of ions and small molecules across the cell membrane, and the recognition of ligands by receptors and signalling across the membrane.

It is possible to remove membrane proteins from their native environment through the use of detergents. Detergents have a general molecular structure similar to that of the phospholipids of the membrane bilayer, with a hydrophilic polar head and a hydrophobic tail. As such, they are able to bind to both the hydrophobic and hydrophilic regions of the membrane protein, and solubilise the protein in water. This allows the many different proteins to be separated using standard chromatographic techniques, and opens up the possibility of characterisation (e.g. through standard sequencing methods) of the proteins. One such method of protein extraction is described in U.S. Pat. No. 5,763,586.

However, it is to be expected that the detergent will affect the conformation of the protein, given the differences in structure between the detergent and the lipid bilayer. Indeed, denaturing of proteins in detergents such as SDS is often desirable in order to carry out assessment of molecular weight and other characterisation. However, any such loss in native conformation will lead to a loss in function. As such, solubilisation in detergent does not provide a reliable method for determining native protein function.

GPCRs, in particular, are generally unstable when isolated and very few, such as bovine rhodopsin (which is exceptionally stable), have proven amenable to crystallisation. The lack of a general method to solubilise and characterise stable and active membrane proteins has frustrated efforts to define and exploit their mechanisms.

Attempts have been made to solubilise membrane proteins in an environment which more closely approximates to that of the native membrane, but which still allows chromatographic separation and characterisation.

For example, published UK patent application GB 2 445 013 describes a macromolecular assembly of a surfactant and a lipid, where the assembly is less than 100 nm in diameter. These assemblies are thought to be bilayer discs. The assemblies are stated to be useful for the solubilisation of membrane proteins, by dialysis of a solution of the assemblies (without proteins) and detergent-stabilised proteins. The protein-containing assemblies may then be used for screening candidates for interaction with the protein.

Similarly, published international (PCT) patent application WO 2006/129127 discloses a macromolecular assembly of copolymer of styrene and maleic acid (in the ratio of at least 1:1) in combination with a (synthetic) lipid. Formation of assemblies incorporating membrane protein, by adding a solution of the polymer to purified protein stabilised in synthetic lipid, or by adding purified protein to polymer/lipid assemblies, is also disclosed.

There is therefore a need for a mechanism of solubilisation of membrane proteins in a manner which retains characteristics of the native membrane environment.

According to a first aspect of the invention there is provided a method for solubilising a membrane protein, comprising providing cellular material comprising the membrane protein and an associated membrane lipid, providing a copolymer of styrene and maleic acid wherein the styrene:maleic acid ratio is between 1:2 and 10:1, and mixing the copolymer with the cellular material to cause the copolymer, lipid and protein to form macromolecular assemblies.

It will be understood that, in this context, the 'associated membrane lipid' should be derived from the same source as the membrane protein. In some embodiments, providing cellular material comprises providing cellular material which is free from added lipid.

It has been surprisingly found by the inventors that membrane proteins can be extracted from cellular material and incorporated into the macromolecular assemblies without the need for initial purification of the protein. Without wishing to be bound by theory, it is believed that the formation of macromolecular assemblies in which the protein is incorporated together with lipid from the protein's native environment, without initial purification of the protein, maximises the likelihood of retaining the protein in its native conformation. Thus, the method enables a more accurate assessment of native protein function and characteristics.

In some embodiments, providing a copolymer of styrene and maleic acid comprises providing a copolymer of styrene and maleic anhydride, and hydrolysing the maleic anhydride to maleic acid. Copolymers of styrene and maleic anhydride are available from Sartomer Company Inc., Exton Pa., USA under the trade names SMA® 2000 and SMA® 3000. Suitable hydrolysis methods are known in the art.

In some embodiments, providing cellular material comprising the membrane protein and associated membrane lipid comprises providing whole cells.

It is believed that, by enabling the formation of macromolecular assemblies in which the protein retains its native conformation, the ability of the protein to retain bound ligand is increased. Thus, the resulting macromolecular assembly can be used to provide insight into the interaction between the protein and ligand, and hence into the protein function.

In some further embodiments, the method further comprises treating the macromolecular assemblies to digest or remove other cellular components.

In some alternative embodiments, providing cellular material comprising the membrane protein and associated membrane lipid comprises providing purified membrane material. Such purified membrane material may be partly or at least substantially free from other cellular material, such as for example nucleic acids. For example, providing purified membrane material may comprise centrifugation of lysed cells in a manner known in the art.

It has been found that the presence of DNA in a solution of macromolecular assemblies can increase viscosity and lead to difficulties in purification. Thus, it is advantageous to ensure that the macromolecular assemblies produced by the present method are at least substantially free from nucleic acid, either by separating the membrane material from other cellular components before macromolecular assembly, or by treatment of the liquid containing the assemblies.

In some embodiments, providing cellular material comprising the membrane protein and an associated membrane lipid comprises providing cellular material comprising the membrane protein, a ligand bound to the protein and an associated membrane lipid; and mixing the copolymer with the cellular material to cause the copolymer, lipid and protein to form macromolecular assemblies comprises mixing the copolymer with the cellular material to cause the copolymer, lipid protein and ligand to form macromolecular assemblies.

In some embodiments, providing a copolymer of styrene and maleic acid wherein the styrene:maleic acid ratio is between 0.5:1 and 10:1 comprises providing a copolymer of styrene and maleic acid wherein the styrene:maleic acid ratio is between 1:1 and 5:1. In some further embodiments, the styrene:maleic acid ratio is between 1.5:1 and 4:1, or between 2:1 and 3:1.

It will be understood that, due to the nature of polymerisation processes, such monomer ratios are bulk averages, and are not to be taken as descriptive of a particular molecular structure having defined arrangements of monomers. Nevertheless, in general it is to be expected that the monomer types are distributed throughout the copolymer.

In some embodiments, providing a copolymer of styrene and maleic acid comprises providing a copolymer of styrene and maleic acid having a molecular weight of between 3000 Da and 120000 Da. In some further embodiments, the copolymer has a molecular weight of between 5000 Da and 15000 Da. In some still further embodiments, the copolymer has a molecular weight of between 7000 and 10000 Da.

In some embodiments, mixing the copolymer with the cellular material to cause the copolymer, lipid and protein to form macromolecular assemblies comprises mixing the copolymer with the cellular material at a pH of between 6 and 9. In some further embodiments, mixing the copolymer with the cellular material to cause the copolymer, lipid and protein to form macromolecular assemblies comprises mixing the copolymer with the cellular material at a pH of between 6.5 and 8.5. In still further embodiments, mixing the copolymer with the cellular material to cause the copolymer, lipid and protein to form macromolecular assemblies comprises mixing the copolymer with the cellular material at a pH of between 7 and 8.

In some embodiments, the method further comprises purifying the macromolecular assemblies. For example, the method may comprise chromatographic purification of the macromolecular assemblies. Where it is desired to isolate assemblies of a specific membrane protein which has been genetically engineered to include a purification tag (such as multiple histidine residues, or a glutathione S-transferase enzyme), the macromolecular assemblies can be purified by any method appropriate to the particular purification tag used, such as for example affinity chromatography. Other protein purification techniques well known in the art may also be used, as will be readily appreciated by the person skilled in the art.

In some embodiments, providing a copolymer of styrene and maleic acid comprises providing a copolymer of styrene and maleic acid which has been labelled to aid in identification. Suitable labels include, for example, fluorescent materials and radioisotopes.

In some embodiments, mixing the copolymer with the cellular material is carried out at a temperature of at least 15° C. or at least 20° C. Additionally or alternatively, mixing the copolymer with the cellular material may be carried out at a temperature no lower than the gel to liquid phase transition temperature of the cellular material.

It is well known in biochemical research that, when working with proteins (and particularly where it is desired to maintain the proteins in their native conformations), any processing should be carried out at low temperature. Thus, processing of proteins (such as extraction) is commonly performed in a refrigerated room. The purpose of operation at low temperature is to prevent any degradation of the protein, including (but not limited to) denaturation and oxidation. However, at such low temperatures, cellular material has a tendency to form a gel-like structure, with the result that the processing is difficult to achieve and takes longer than desired.

It has surprisingly been found by the present inventors that the method of the invention stabilises the protein to such an extent that processing can be carried out at higher temperatures. In particular, processing can be carried out at or above the gel to liquid phase transition temperature, thereby reducing the time required to solubilise the protein (in the form of the macromolecular assemblies) without sacrificing the protein stability.

The gel to liquid phase transition temperature is well understood by those in the art, and is known to be affected by the acyl chain lengths in the phospholipids of a phospholipid bilayer. Many lipids in bacteria and humans have chain lengths of between 12 and 14 carbon atoms, giving a transition temperature of between 20 and 40° C.

In some further embodiments, mixing the copolymer with the cellular material additionally comprises sonication of the mixture. This aids in mixing of the cellular material with the copolymer by breaking up membranes in the cellular material.

According to a second aspect of the invention, there is provided a macromolecular assembly producible according to the method of the first aspect of the invention.

According to a third aspect of the invention, there is provided a macromolecular assembly comprising a copolymer of styrene and maleic acid wherein the styrene:maleic acid ratio is between 1:2 and 10:1, a membrane protein, and an associated membrane lipid.

It will be understood that, in this context, the 'associated membrane lipid' should be a membrane lipid which, in a native cell, is found in the same membrane as the membrane protein.

In some embodiments, the associated membrane lipid is a membrane lipid which, in a native cell, surrounds the membrane protein to form a native protein-lipid complex.

In some embodiments, the copolymer of styrene and maleic acid has a styrene:maleic acid ratio between 1:1 and 5:1. In some further embodiments, the styrene:maleic acid ratio is between 1.5:1 and 4:1, or between 2:1 and 3:1.

It will be understood that, due to the nature of polymerisation processes, such monomer ratios are bulk averages, and are not to be taken as descriptive of a particular molecular structure having defined arrangements of monomers. Nevertheless, in general it is to be expected that the monomer types are distributed throughout the copolymer.

In some embodiments, the copolymer of styrene and maleic acid has a molecular weight of between 3000 Da and 12000 Da. In some further embodiments, the copolymer has a molecular weight of between 5000 Da and 15000 Da. In some still further embodiments, the copolymer has a molecular weight of between 7000 and 10000 Da.

In some embodiments, the copolymer of styrene and maleic acid is labelled to aid in identification. Suitable labels include, for example, fluorescent materials and radioisotopes.

The macromolecular assemblies of the second and third aspects of the invention are believed to have a number of applications. In addition to dissolution and chromatographic separation of membrane proteins in their native lipid environments, the assemblies can be used to purify intact naturally-occurring oligomers (such as dimers) of such proteins, investigate binding of such proteins to ligands (including agonists and antagonists), and observe such binding by means of mass spectroscopy. In particular, assemblies containing GPCRs may be useful for such purposes.

Examples of aspects of the invention are described below, with reference to the accompanying Figures, in which.

PREPARATION OF SMA COPOLYMER—METHOD 1

Figure 1:
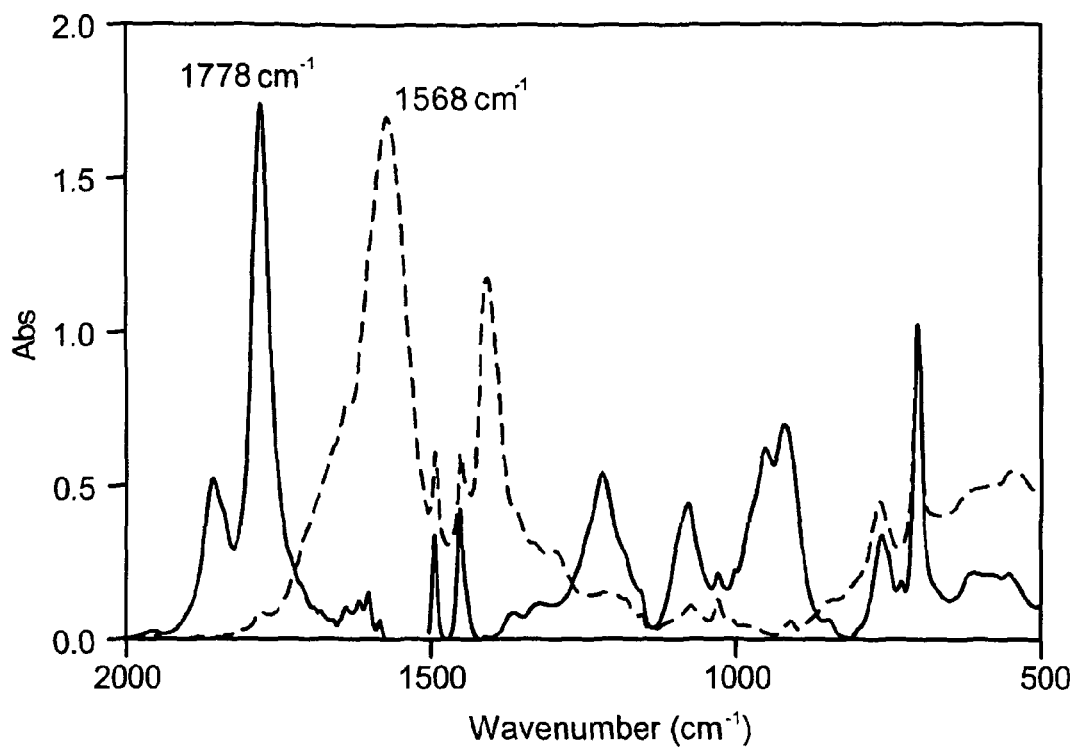
FIG. 1 shows FTIR spectra of the styrene:maleic anhydride (acid) copolymer before (solid line) and after (dashed line) hydrolysis.

Low molecular weight styrene:maleic anhydride copolymer with a 2:1 monomer ratio (commercially available as SMA® 2000P from Sartomer Europe, Paris, France) was solubilised in 1.0 M sodium hydroxide, and refluxed for two hours followed by incubation at 4° C. for 48 hours, to give a 5% stock solution of the corresponding styrene:maleic acid copolymer. Completion of the reaction was confirmed by Fourier transform infrared (FTIR) spectroscopic analysis of the lyophilized product (FIG. 1). It can be seen that the anhydride carbonyl peak at 1778 cm$^{-1}$ has been replaced by the carboxylate carbonyl peak at 1568 cm$^{-1}$. Subsequently the sample was dialyzed extensively in 50 mM Tris pH8 to remove any traces of sodium hydroxide.

PREPARATION OF SMA COPOLYMER—METHOD 2

10% (w/v) powdered SMA® 2000P (as for method 1) was refluxed for 2 hours ion 1 M NaOH. The polymer was left to cool to 4° C. then stored for 2 days until hydrolysis was complete as estimated by IR analysis. The polymer was then precipitated by addition of HCl to give a pH below 3. The resulting suspension was centrifuged at 6000×g for 10 minutes, and the supernatant removed. The polymer was then resuspended and washed with H$_2$O. Centrifugation, separation and washing were repeated twice more, and the polymer was then resuspended in H$_2$O and the pH adjusted to greater than 7 to resolubilise the polymer. The polymer solution was dialysed against H$_2$O for 2 days to remove any further contamination, then frozen and freeze dried.

COMPARATIVE EXAMPLE

Formation of Macromolecular Assemblies from Purified Polymer

Unlabelled PagP protein was expressed in *Escherichia coli* as cytoplasmic inclusion bodies using the pETCrcAHΔS plasmid (Bishop et al (2000) EMBO J 19:5071-5080) and purified as described in Hwang et al (2002) Proc. Natl. Acad. Sci. USA 99(21):13560-5. The precipitated PagP was dissolved in 5% SDS and dialyzed (molecular mass cutoff of 3500 kDa) for 5 days against 50 mM Tris pH8 to remove excess SDS. The resulting sample contained 0.5 mM PagP. Solid n-octyl-β-D-glucoside (β-OG) was then slowly dissolved to a final concentration of 100 mM, and ethanol was added to 1%. Dimyristoylphosphatidylcholine (DMPC) was added to a final concentration of 2% (w/v) and stirred until completely solubilised. Biobead SM-2 nonpolar polystyrene adsorbents were added at twice the manufacturer's specifications in order to remove β-OG detergent, and then left mixing at 4° C. for 16 hours. This process was repeated until an opaque lipid solution was produced composed of multilamellar vesicles (MLVs).

The solution was brought up to room temperature and 5% styrene:maleic acid (SMA) copolymer solution in 40 mM Tris pH8 was added to 1:1 (v/v) and left stirring until the solution cleared. Excess copolymer/lipid was then removed using standard HisTrap purification procedures (GE Healthcare).

EXAMPLE 1

Formation of Macromolecular Assemblies from *E. Coli* Membrane

A construct of PagP containing its N-terminal signal peptide was incorporated into the pET21b expression vector (Novagen) and overexpressed into the outer membrane of *Escherichia coli* strain BL21(DE3) (Novagen) as a C-terminally His-tagged fusion protein using standard molecular biology techniques. Cells were grown in Luria broth (LB) media with selection for ampicillin resistance (100 μg/ml) at 37° C. until reaching an OD$_{600}$ 0.4, at which point the temperature was reduced to 18° C. Expression was induced by addition of 1 mM IPTG when an optical density at 600 nm of 0.6 was reached. After 16 h, cell pellets were harvested by centrifugation at 6000×g for 15 minutes. Cells were resuspended in 50 mM tris(hydroxymethyl)aminomethane (Tris) buffer pH8, 1 M NaCl, and Complete Protease Inhibitor (Roche) before being lysed by an Emulsiflex C3 (Avestin). The cell lysate was centrifuged at 5000×g to remove cell debris, before the supernatant was then centrifuged at 75000×g for 1 hour to pellet the membrane fraction.

Raw membrane was resuspended in 50 mM Tris pH8+1 M NaCl+10% glycerol (approximately 20 ml per 2 L *E. coli* culture) at 4° C. to give a final protein concentration of between 20-40 mg/ml, as estimated by absorbance at 280 nm. An equal volume of 5% (w/v) hydrolysed SMA 2000P copolymer in 50 mM Tris pH8+1 M NaCl+10% glycerol was added to the sample (to give a final concentration of 2.5% w/v) as well as 1% w/v DMPC (1,2-dimyristoyl-sn-glycero-3-phosphocholine) (Avanti Polar Lipids). The solution was placed on a rocking platform and allowed to mix gently at 20° C. until all of the DMPC had dissolved (approximately 1-2 hours). The resulting solution was centrifuged at 75000×g for 1 hour at 4° C. to remove unincorporated material, leaving the *E. coli* membrane protein copolymer assemblies in solution.

The protein copolymer assemblies were purified by standard metal chelate chromatography (Crowe et al (1994) *Methods Mol. Biol.* 31 371-387) using either a 5 ml HisTrap (GE Healthcare) column or 5 ml $Co^{2+}$ IPAP (GE Healthcare) column. The raw assembly solution was loaded at a rate of 0.2 ml/min to maximise binding. The column was washed with 5 column volumes to remove non-specifically bound contaminants, and the purified protein copolymer assemblies eluted in 1 ml fractions using 50 mM Tris pH 8+1 M NaCl+50 mM EDTA.

EXAMPLE 2

Formation of Molecular Assemblies from *Pichia* Membrane

*Pischia pastoris* transformants were cultured in growth media overnight and protein production was induced by addition of methanol. Samples were collected by centrifugation after induction, supernatants were decanted and cell pellets were frozen. *Pichia* membrane was prepared from cells by resuspension in 50 mM Tris pH 8+50 mM NaCl, followed by cell disruption using an Emulsiflex C3 cell disrupter (Avestin) and centrifugation at 100000×g for 1 hr.

Raw membrane was resuspended in 50 mM Tris pH 8+50 mM NaCl at 4° C. to give a final membrane concentration of 6% w/v. An equal volume of hydrolysed SMA polymer (5% w/v) in 50 mM Tris pH 8+50 mM NaCl was added to give a final concentration of 2.5% (w/v). The sample was left shaking at 20° C. for 5 minutes to enable assembly formation to occur. Insoluble/unincorporated material was removed by centrifugation at 75000×g for 30 minutes leaving the raw *Pichia* membrane protein copolymer assemblies in solution.

EXAMPLE 3

*Pichia* Membrane Loading

Figure 2:
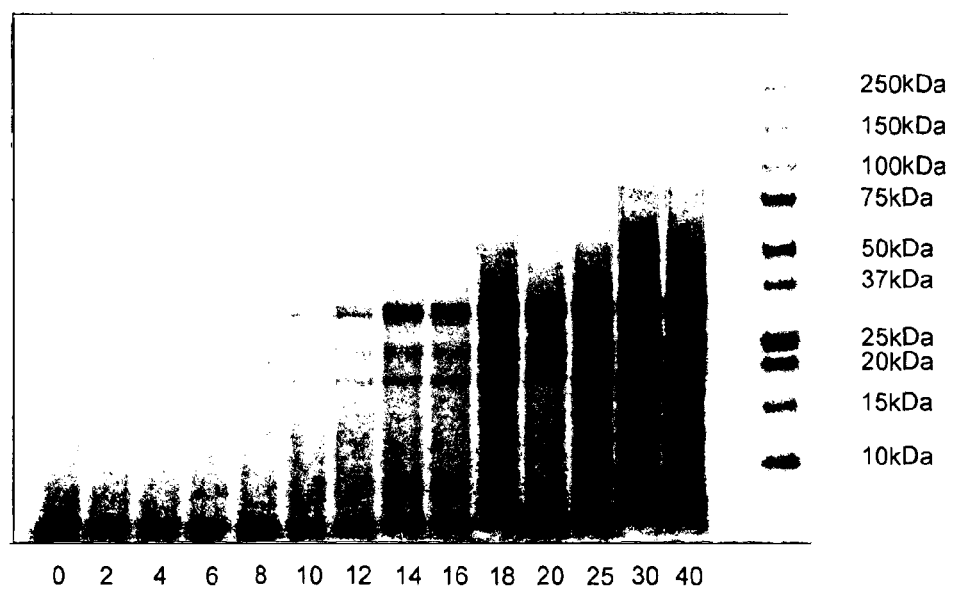
FIG. 2 shows SDS-polyacrylamide gel electrophoresis of assembly formation using increasing concentrations of *Pichia* membrane material.

*Pichia* membrane was isolated as for Example 2. Raw membrane was resuspended in 50 mM Tris pH 8+50 mM NaCl at 4° C. to give a range of concentrations from 0-400 mg per ml of sample (0-40% w/v). An equal volume of hydrolysed SMA polymer (5% w/v) in 50 mM Tris pH 8+50 mM NaCl was added to each sample to give a final concentration of 2.5% (w/v). The samples were left shaking at 20° C. for 5 minutes to enable assembly formation to occur. Insoluble/ unincorporated material was removed by centrifugation at 75000×g for 30 minutes, leaving the raw *Pichia* membrane protein copolymer assemblies in solution. The results are shown in FIG. 2.

EXAMPLE 4

Formation and Purification of Molecular Assemblies from *Pichia* Membrane

*Pichia* membrane was isolated as for Example 2. Raw membrane was resuspended in solubilisation buffer (50 mM Tris-HCl, 10% glycerol, 500 mM NaCl, 2.5% (w/v) hydrolysed SMA polymer (hSMA), 1% DMPC (Avanti) at pH 8). The slurry was stirred for one to two hours at room temperature and then centrifuged at 150,000×g in a Beckman Type 70.1 Ti Rotor for 45 min. The supernatant containing solubilised overexpressed human Ata adenosine receptor (hA2aR) was reserved for further use.

Purification was carried out at 0-4° C. The supernatant containing the solubilised hA2aR was diluted with 80 mM imidazole in the re-suspension buffer (50 mM Tris-HCl, 10% glycerol, 500 mM NaCl, pH 8) so that the mixture had a final concentration of 20 mM imidazole in the re-suspension buffer. The sample was incubated with $Ni^{2+}$-NTA resin (Qiagen) with slow rotation overnight. Typically, 1.5 ml of resin was used for a 20 g cell pellet from the original culture. The resin was washed with 5 times the resin volume of wash buffer (the re-suspension buffer, plus 60 mM imidazole, at pH 8), before the receptor was eluted using an elution buffer (the re-suspension buffer plus 250 mM imidazole, at pH 8) within 20 times the resin volume.

Figure 3:
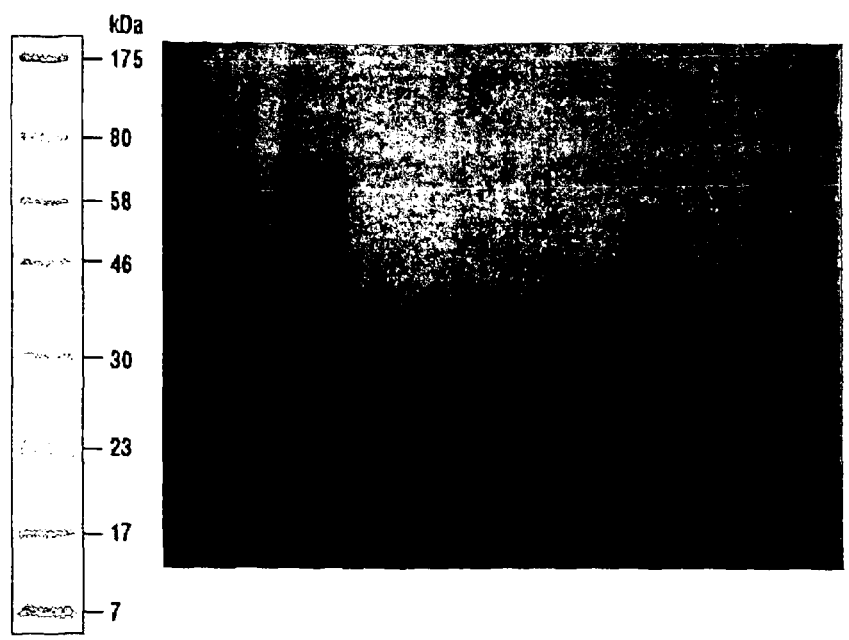
FIG. 3 shows SDS-polyacrylamide gel electrophoresis of purified human A2a adenosine receptor (hA2aR) assemblies after successive washing steps during resin purification.

The fractions containing the hA2aR were concentrated using Vivapin 20 concentrator (30 kDa cut off, Sigma-Aldrich), and washed extensively with gel filtration elution buffer (50 mM Tris-HCl, 10% glycerol, 150 mM NaCl, at pH 8) before injecting into a Superdex 200 10/300 GL column attached to an ÄKTA™ purifier FPLC purification system (GE Healthcare). The fractions were eluted with gel filtration elution buffer (50 mM Tris-HCl, 10% glycerol, 150 mM NaCl, at pH 8). The results are shown in FIG. 3.

EXAMPLE 5

Figure 4:
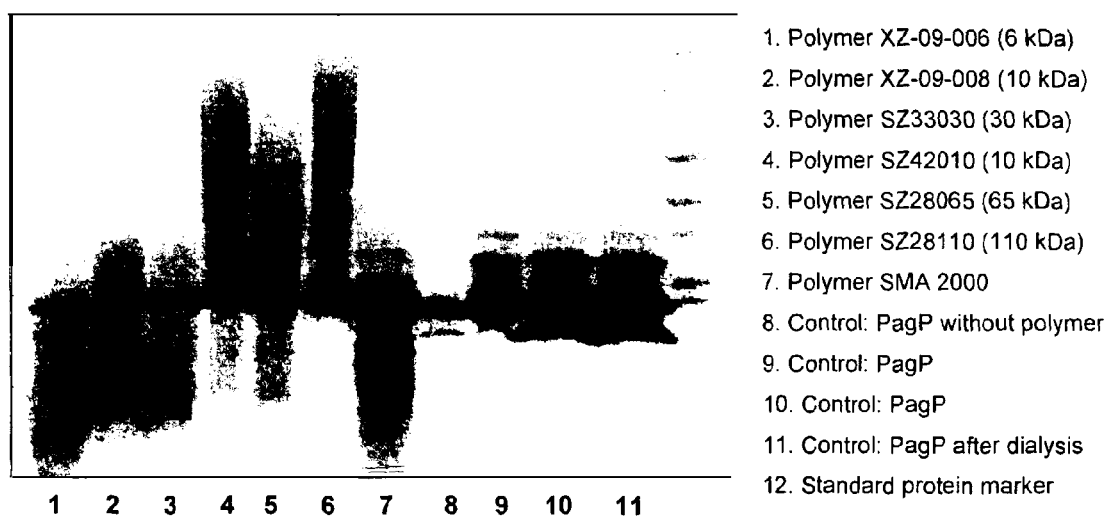
FIG. 4 shows SDS-polyacrylamide gel electrophoresis of purified PagP assemblies formed using different molecular weight polymers.

Formation of Macromolecular Assemblies from *E. Coli* Membrane Using Polymers with a Range of Molecular Weights The following styrene:maleic anhydride copolymers (with a monomer ratio of 2:1, as above) (commercially available from Polyscope Polymers, Holland) were used: XZ-09-006 (6 kDa); XZ-09-008 (10 kDa); SZ33030 (30 kDa); SZ42010 (10 kDa); SZ28065 (65 kDa) and SZ28110 (110 kDa). Polymers were prepared as per method 2, except that the polymers were dialysed against 0.1M Tris pH8 instead of water. The polymers were found to have higher purity levels than those obtained from Sartomer SMA® 200P (as measured by dilution following dialysis PagP was expressed and the molecular assemblies were purified according to the protocol described in Example 1. The results are shown in FIG. 4. Macromolecular assebly formation was slower than with the polymers obtained from Sartomer SMA® 2000P. In particular, Macromolecular assembly formation was slowest with higher molecular weight polymers. The macromolecular assemblies appeared to be stable for at least 3 days at room temperature.

The invention claimed is:

1. A method for solubilising a membrane protein, comprising providing cellular material comprising the membrane protein and an associated membrane lipid, providing a copolymer of styrene and maleic acid wherein the styrene:maleic acid ratio is between 1:2 and 10:1, and mixing the copolymer with the cellular material without initial purification of the membrane protein to cause the copolymer, lipid and protein to form soluble macromolecular assemblies wherein the native conformation of the membrane protein is retained.

2. The method as claimed in claim 1, wherein providing cellular material comprises providing cellular material which is free from added lipid.

3. The method as claimed in claim 1, wherein providing a copolymer of styrene and maleic acid comprises providing a copolymer of styrene and maleic anhydride, and hydrolysing the maleic anhydride to maleic acid.

4. The method as claimed in claim 1, wherein providing cellular material comprising the membrane protein and associated membrane lipid comprises providing whole cells.

5. The method as claimed in claim 1, further comprising treating a solution of macromolecular assemblies to digest or remove other cellular components.

6. The method as claimed in claim 1, wherein providing a copolymer of styrene and maleic acid wherein the styrene:maleic acid ratio is between 0.5:1 and 10:1 comprises providing a copolymer of styrene and maleic acid wherein the styrene:maleic acid ratio is between 1:1 and 5:1.

7. The method as claimed in claim 6, wherein providing a copolymer of styrene and maleic acid wherein the styrene:maleic acid ratio is between 0.5:1 and 10:1 comprises providing a copolymer of styrene and maleic acid wherein the styrene:maleic acid ratio is between 2:1 and 3:1.

8. The method as claimed in claim 1, wherein providing a copolymer of styrene and maleic acid comprises providing a copolymer of styrene and maleic acid having a molecular weight of between 3000 Da and 120000 Da.

9. The method as claimed in claim 1, further comprising purifying the macromolecular assemblies.

10. A macromolecular assembly producible according to claim 1.

11. A macromolecular assembly comprising a copolymer of styrene and maleic acid wherein the styrene:maleic acid ratio is between 1:2 and 10:1, a membrane protein, and an associated membrane lipid, wherein the native conformation of the membrane protein is retained.

12. The macromolecular assembly as claimed in claim 11, wherein the copolymer of styrene and maleic acid has a styrene:maleic acid ratio between 2:1 and 3:1.

13. The macromolecular assembly as claimed in claim 10 or 11, wherein the copolymer of styrene and maleic acid has a molecular weight of between 3000 Da and 120000 Da.

* * * * *